(12) United States Patent
Ashley

(10) Patent No.: US 6,283,960 B1
(45) Date of Patent: Sep. 4, 2001

(54) APPARATUS FOR DELIVERY OF ENERGY TO A SURGICAL SITE

(75) Inventor: John Ashley, San Francisco, CA (US)

(73) Assignee: Oratec Interventions, Inc., Menlo Park, CA (US)

(*) Notice: Subject to any disclaimer, the term of this patent is extended or adjusted under 35 U.S.C. 154(b) by 0 days.

(21) Appl. No.: 09/047,182

(22) Filed: Mar. 19, 1998

Related U.S. Application Data

(63) Continuation-in-part of application No. PCT/US97/19189, filed on Oct. 22, 1997, which is a continuation-in-part of application No. 08/881,525, filed on Jun. 24, 1997, now Pat. No. 6,122,549, and a continuation-in-part of application No. 08/881,692, filed on Jun. 24, 1997, now Pat. No. 6,073,051, and a continuation-in-part of application No. 08/881,527, filed on Jun. 24, 1997, now Pat. No. 5,980,504, and a continuation-in-part of application No. 08/881,693, filed on Jun. 24, 1997, now Pat. No. 6,007,570, and a continuation-in-part of application No. 08/881,694, filed on Jun. 24, 1997, now Pat. No. 6,095,149, application No. 09/047,182, which is a continuation of application No. 08/888,359, filed on Jul. 3, 1997, and a continuation of application No. 08/714,987, filed on Sep. 17, 1996, and a continuation of application No. 08/696,051, filed on Aug. 13, 1996, and a continuation of application No. 08/637,095, filed on Apr. 24, 1996, and a continuation of application No. 08/547,510, filed on Oct. 24, 1995, now Pat. No. 5,785,705

(60) Provisional application No. 60/029,735, filed on Oct. 23, 1996, provisional application No. 60/029,600, filed on Oct. 23, 1996, provisional application No. 60/029,734, filed on Oct. 23, 1996, provisional application No. 60/029,602, filed on Oct. 23, 1996, provisional application No. 60/046,001, filed on May 8, 1997, provisional application No. 60/047,820, filed on May 28, 1997, provisional application No. 60/047,681, filed on May 28, 1997, provisional application No. 60/045,941, filed on May 8, 1997, provisional application No. 60/047,818, filed on May 28, 1997, provisional application No. 60/047,848, filed on May 28, 1997, and provisional application No. 60/046,002, filed on May 8, 1997.

(51) Int. Cl.[7] .................................................. A61B 18/04

(52) U.S. Cl. ................................. 606/32; 606/34; 607/99; 607/116

(58) Field of Search .............................. 607/96–102, 113, 607/116–117, 148, 149; 600/373; 606/27, 32, 41–42, 34

(56) References Cited

U.S. PATENT DOCUMENTS 2,090,923    8/1937    Wappler .......................... 128/303.15

(List continued on next page.)

FOREIGN PATENT DOCUMENTS 0 257 116 A1    3/1988    (EP) ................................. A61N/1/36

(List continued on next page.)

OTHER PUBLICATIONS

Auhli, Richard A., "The Use of the Resectoscope in Gynecology." Biomedical Business International, Oct. 11, 1990, pp. 91–93.

(List continued on next page.)

*Primary Examiner*—John P. Lacyk
*Assistant Examiner*—Ryan Carter
(74) *Attorney, Agent, or Firm*—Wilson, Sonsini, Goodrich & Rosati

(57) ABSTRACT

An apparatus for delivering energy to a surgical site from an energy source is provided. The apparatus includes; a handle, an actuator, a shaft, and a deflection wire. The actuator is movably coupled to the handle. The actuator moves from a first position to a second position. The shaft includes a proximal end, a deflectable portion and an energy delivery portion. The proximal end of the shaft is coupled to the handle. The energy delivery portion is coupled to the energy source to deliver energy to the surgical site. The deflection wire includes a proximal portion and a distal portion. The distal portion is affixed to the shaft. The proximal portion is affixed to the actuator. A movement of the actuator from the first position to the second position moves the deflection wire to produce a deflection of the deflectable portion. In an alternate embodiment of the invention a sensor and feedback control module are provided.

11 Claims, 8 Drawing Sheets

U.S. PATENT DOCUMENTS

| | | | |
|---|---|---|---|
| 3,178,728 | 4/1965 | Christensen | 3/1 |
| 3,579,643 | 5/1971 | Morgan | 3/1 |
| 3,776,230 | 12/1973 | Neefe | 128/260 |
| 3,856,015 | 12/1974 | Iglesias | 128/303.15 |
| 3,867,728 | 2/1975 | Substad et al. | 3/1 |
| 3,879,767 | 4/1975 | Substad | 3/1 |
| 3,886,600 | 6/1975 | Kahn et al. | 3/1 |
| 3,938,198 | 2/1976 | Kahn et al. | 3/1.912 |
| 3,945,375 | 3/1976 | Banko | 128/6 |
| 3,987,499 | 10/1976 | Scharbach et al. | 3/1.91 |
| 3,992,725 | 11/1976 | Homsy | 3/1 |
| 4,043,342 | 8/1977 | Morrison, Jr. | 128/303.14 |
| 4,074,718 | 2/1978 | Morrison, Jr. | 128/303.14 |
| 4,085,466 | 4/1978 | Goodfellow et al. | 3/1.91 |
| 4,129,470 | 12/1978 | Homsy | 156/155 |
| 4,134,406 | 1/1979 | Iglesias | 128/303.15 |
| 4,224,696 | 9/1980 | Murray et al. | 3/1.911 |
| 4,224,697 | 9/1980 | Murray et al. | 3/1.911 |
| 4,326,529 | 4/1982 | Doss et al. | 128/303.1 |
| 4,344,193 | 8/1982 | Kenny | 3/1.911 |
| 4,362,160 | 12/1982 | Hiltebrandt | 128/303.15 |
| 4,375,220 | 3/1983 | Matvias | 128/804 |
| 4,381,007 | 4/1983 | Doss | 128/303.1 |
| 4,397,314 | 8/1983 | Vaguine | 128/399 |
| 4,476,862 | 10/1984 | Pao | 128/303.17 |
| 4,483,338 | 11/1984 | Bloom et al. | 128/303.13 |
| 4,517,965 | 5/1985 | Ellison | 128/20 |
| 4,517,975 | 5/1985 | Garito et al. | 128/303.13 |
| 4,590,934 | 5/1986 | Malis et al. | 128/303.14 |
| 4,593,691 | 6/1986 | Lindstrom et al. | 128/303.14 |
| 4,597,379 | 7/1986 | Kihn et al. | 128/1 R |
| 4,601,705 | 7/1986 | McCoy | 604/94 |
| 4,651,734 | 3/1987 | Doss et al. | 128/303.14 |
| 4,811,733 | 3/1989 | Borsanyi et al. | 128/303.14 |
| 4,815,462 | 3/1989 | Clark | 128/305 |
| 4,838,859 | 6/1989 | Strassmann | 604/95 |
| 4,846,175 | 7/1989 | Frimberger | 128/303.15 |
| 4,873,976 | 10/1989 | Schreiber | 128/334 R |
| 4,894,063 | 1/1990 | Nashef | 623/13 |
| 4,895,148 | 1/1990 | Bays et al. | 606/213 |
| 4,907,585 | 3/1990 | Schachar | 606/28 |
| 4,907,589 | 3/1990 | Cosman | 606/34 |
| 4,924,865 | 5/1990 | Bays et al. | 606/77 |
| 4,944,727 | 7/1990 | McCoy | 604/95 |
| 4,950,234 | 8/1990 | Fujioka et al. | 604/60 |
| 4,955,882 | 9/1990 | Hakky | 606/14 |
| 4,966,597 | 10/1990 | Cosman | 606/50 |
| 4,976,709 | 12/1990 | Sand | 606/5 |
| 4,976,715 | 12/1990 | Bays et al. | 606/77 |
| 4,998,933 | 3/1991 | Eggers et al. | 606/41 |
| 5,007,908 | 4/1991 | Rydell | 606/47 |
| 5,009,656 | 4/1991 | Reimels | 606/48 |
| 5,085,657 | 2/1992 | Ben-Simhon | 606/42 |
| 5,085,659 | 2/1992 | Rydell | 606/47 |
| 5,098,430 | 3/1992 | Fleenor | 606/42 |
| 5,100,402 | 3/1992 | Fan | 606/41 |
| 5,103,804 | 4/1992 | Abele et al. | 128/4 |
| 5,114,402 | 5/1992 | McCoy | 604/95 |
| 5,152,748 | 10/1992 | Chastagner | 604/95 |
| 5,178,620 | 1/1993 | Eggers et al. | 606/41 |
| 5,186,181 | 2/1993 | Franconi et al. | 128/804 |
| 5,191,883 | 3/1993 | Lennox et al. | 128/401 |
| 5,192,267 | 3/1993 | Shapira et al. | 604/22 |
| 5,201,729 | 4/1993 | Hertmann et al. | 606/2 |
| 5,201,730 | 4/1993 | Easley et al. | 606/4 |
| 5,201,731 | 4/1993 | Hakky | 606/15 |
| 5,213,097 | 5/1993 | Zeindler | 128/401 |
| 5,230,334 | 7/1993 | Klopotek | 128/399 |
| 5,242,439 | 9/1993 | Larsen et al. | 606/15 |
| 5,242,441 * | 9/1993 | Avitall | 600/374 X |
| 5,261,906 | 11/1993 | Pennino et al. | 606/46 |
| 5,267,994 | 12/1993 | Gentelia et al. | 606/15 |
| 5,275,151 | 1/1994 | Shockey et al. | 128/4 |
| 5,279,559 | 1/1994 | Barr | 604/95 |
| 5,284,479 | 2/1994 | de Jong | 604/60 |
| 5,304,169 | 4/1994 | Sand | 606/5 |
| 5,308,311 | 5/1994 | Eggers et al. | 606/28 |
| 5,311,858 | 5/1994 | Adair | 128/4 |
| 5,320,115 | 6/1994 | Kenna | 128/898 |
| 5,323,778 | 6/1994 | Kandarpa et al. | 128/653.2 |
| 5,334,193 | 8/1994 | Nardella | 606/41 |
| 5,342,357 | 8/1994 | Nardella | 606/40 |
| 5,348,554 | 9/1994 | Imran et al. | 606/41 |
| 5,352,868 | 10/1994 | Denen et al. | 219/501 |
| 5,354,331 | 10/1994 | Schachar | 623/4 |
| 5,364,395 | 11/1994 | West, Jr. | 606/46 |
| 5,366,443 | 11/1994 | Eggers et al. | 604/114 |
| 5,366,490 | 11/1994 | Edwards et al. | 607/99 |
| 5,382,247 | 1/1995 | Cimino et al. | 606/33 |
| 5,397,304 | 3/1995 | Truckai | 604/95 |
| 5,401,272 | 3/1995 | Perkins | 606/15 |
| 5,415,633 | 5/1995 | Lazarus et al. | 604/95 |
| 5,423,806 | 6/1995 | Dale et al. | 606/15 |
| 5,433,739 | 7/1995 | Sluijter et al. | 607/99 |
| 5,437,661 | 8/1995 | Rieser | 606/15 |
| 5,437,662 | 8/1995 | Nardella | 606/40 |
| 5,451,223 | 9/1995 | Ben-Simhon | 606/42 |
| 5,458,596 | 10/1995 | Lax et al. | 606/31 |
| 5,464,023 | 11/1995 | Viera | 128/772 |
| 5,465,737 | 11/1995 | Schachar | 128/898 |
| 5,484,403 | 1/1996 | Yoakum et al. | 604/59 |
| 5,484,432 | 1/1996 | Sand | 606/5 |
| 5,484,435 | 1/1996 | Fleenor et al. | 606/46 |
| 5,487,757 | 1/1996 | Truckai et al. | 607/122 |
| 5,498,258 | 3/1996 | Hakky et al. | 606/15 |
| 5,500,012 | 3/1996 | Brucker et al. | 607/122 |
| 5,507,812 | 4/1996 | Moore | 623/13 |
| 5,514,130 | 5/1996 | Baker | 606/41 |
| 5,524,338 | 6/1996 | Martyniuk et al. | 29/825 |
| 5,527,331 | 6/1996 | Kresch et al. | 606/170 |
| 5,542,920 | 8/1996 | Cherif Cheikh | 604/57 |
| 5,569,242 | 10/1996 | Lax et al. | 606/42 |
| 5,599,356 | 2/1997 | Edwards et al. | 606/41 |
| 5,630,839 | 5/1997 | Corbett, III et al. | 607/137 |
| 5,681,282 | 10/1997 | Eggers et al. | 604/114 |
| 5,683,366 | 11/1997 | Eggers et al. | 604/114 |
| 5,688,270 | 11/1997 | Yates et al. | 606/51 |
| 5,697,909 | 12/1997 | Eggers et al. | 604/114 |
| 5,718,702 | 2/1998 | Edwards | 606/41 |
| 5,728,795 | 3/1998 | Bays | 606/22 |
| 5,779,646 * | 7/1998 | Koblish et al. | 600/567 |
| 5,810,809 | 8/1998 | Rydell | 606/49 |

FOREIGN PATENT DOCUMENTS

| | | | |
|---|---|---|---|
| 0 479 482 A1 | 4/1992 | (EP) | A61B/17/39 |
| 0 558 297 A2 | 1/1993 | (EP) | A61M/25/00 |
| 0 572 131 A1 | 1/1993 | (EP) | A61B/17/39 |
| 0 542 412 A1 | 5/1993 | (EP) | A61B/17/39 |
| 0 521 595 A2 | 7/1993 | (EP) | A61M/25/01 |
| 0 682 910 A1 | 11/1995 | (EP) | A61B/1/00 |
| 0 729 730 A1 | 4/1996 | (EP) | A61B/17/32 |
| 0 479 482 B1 | 5/1996 | (EP) | A61B/17/39 |
| 0 737 487 A2 | 10/1996 | (EP) | A61M/25/01 |
| 2 645 008 | 3/1989 | (FR) | A61B/17/32 |
| 1 340 451 | 12/1973 | (GB) | A61F/1/00 |
| 2 164 473 A | 3/1986 | (GB) | A61B/17/36 |
| WO 92/05828 | 4/1992 | (WO) | A61M/25/00 |
| WO 92/10142 | 6/1992 | (WO) | A61B/17/36 |
| WO 93/16648 | 9/1993 | (WO) | A61B/17/32 |
| WO 93/20984 | 10/1993 | (WO) | B26D/1/11 |
| WO 95/01814 | 1/1995 | (WO) | A61N/5/02 |

| | | | |
|---|---|---|---|
| WO 95/20360 | 3/1995 | (WO) | A61B/17/39 |
| WO 95/13113 | 5/1995 | (WO) | A61N/5/02 |
| WO 95/18575 | 7/1995 | (WO) | A61B/17/39 |
| WO95/25471 | 9/1995 | (WO) | A61B/17/39 |
| WO 95/30373 | 11/1995 | (WO) | A61B/17/00 |
| WO 95/30377 | 11/1995 | (WO) | A61B/17/39 |
| WO 95/34259 | 12/1995 | (WO) | A61F/5/48 |
| WO 96/11638 | 4/1996 | (WO) | A61B/17/32 |
| WO 96/32051 | 10/1996 | (WO) | A61B/1/00 |
| WO 96/32885 | 10/1996 | (WO) | A61B/5/04 |
| WO 96/34559 | 11/1996 | (WO) | A61B/5/0402 |
| WO 96/34568 A | 11/1996 | (WO) | A61B/17/36 |
| WO 96/34571 | 11/1996 | (WO) | A61B/17/39 |
| WO 96/39914 | 12/1996 | (WO) | A61B/1/00 |
| WO 97/06855 | 2/1997 | (WO) | A61N/1/40 |
| WO 98/07468 | 2/1998 | (WO) | A61N/1/40 |
| WO 98/17190 | 4/1998 | (WO) | A61B/18/00 |

OTHER PUBLICATIONS

Trimedyne, The Less Invasive Laser Advantage, Omni Spinal Introduction System.

PRNewswire (Dec. 12, 1994), Two Physicians Perform First Outpatient Cervical Disc Procedure Using Laser Technology.

Introduction to the LDD Disc Kit, Oct. 6, 1996.

Mayer et al., Lasers in Percutaneous Disc Surgery: Beneficial Technology or Gimmick?, vol. 25, No.251 (1993) pp. 38–44.

Schatz et al., Preliminary Experience With Percutaneous Laser Disc Decompression in the Treatment of Sciatica, vol. 38, No. 5, Oct. 1995, pp. 432–436.

Savitz M. A., Same–day Microsurgical Arthroscopic lateral–approach Laser–assisted (Small) Fluoroscopic Disectomy, vol. 80, Jun. 1994 pp. 1039–1045.

Bosacco et al., Functional Results of Percutaneous Laser Discectomy, Dec. 1996, pp. 825–828.

Sluijter M.E. The Use of Radiofrequency lesions For Pain Relief in Failed Back Patients, vol. 10 No. 1 (1988).

Cosman et al., Theoretical Aspects of Radiofrequency lesions in the Dorsal Root Entry Zone, vol. 15 No. 6 (1984) pp. 945–950.

Wilkins et al., Neurosurgery: Method of Making Nervous System Lesions, ch. 337, pp. 2490–2499.

Yonezawa et al., The System and Procedure of percutaneous Intradiscal Laser Nucleotomy, vol. 15, No. 5 (1990) pp. 1175–1185.

Gottlob et al., Lasers In Surgery And Medicine: Holmium: YAG Laser Ablation of Human Interverebral Disc: Preliminary Evaluation, vol. 12, (1991) pp. 86–91.

Buchelt et al., Lasers In Surgery And Medicine: Fluorescence Guided Excimer Laser Ablation of Intervertebral Disc In Vitro, vol. 11, (1991) pp. 280–286.

Choy et al., Percutaneous Laser Disc Decompression: A New Therapeutic Modality, vol. 17 No. 8 (1992) pp. 949–956.

Sluijter et al., Presistant Pain, Modern Methods of Treatment: Treatment of Chronic Back and neck Pain, vol. 3, (1981) pp. 141–179.

Sluijter, INT Disabil Studies: The use of Radio Frequency Lesions For Pain Relief in Failed Back, vol. 10, Sep. 4, 1996, pp. 37–43.

Shatz et al., CJS JCC Preliminary Experience With Percutaneous Laser Disc Decompression in the Treatment of Sciatica, vol. 38, No. 5, Oct. 1995 pp. 432–436.

Gerber et al., DER ORTHOPADE: Offene Laserchirurgie am Bewegungsapparat, vol. 25, (1996) pp. 56–63.

Gehring W.J., Exploring the Homeobox (1993), pp. 215–221.

Kelly L.E., Purification and Properties of a 23kDa Ca2+ –binding Protein, (1990) 271, pp. 661–666.

Sluyter, Radiofrequency Lesions in the Treatment of Cervical Pain Syndromes, Radionics, Inc. (1989).

Buchelt et al., Lasers in Surgery and Medicine:Erb:YAG and Hol:YAG Laser Ablation of Meniscus and Intervertebral Discs, vol. 12 No. 4, (1992) pp. 375–381.

Leu et al., DER ORTHOPADE: Endoskopie der Wirbelsaule: Minimal–invasive Therapie, vol. 21, (1992) pp. 267–272.

Phillips et al., JMRI: MR Imaging of Ho: YAG Laser Diskectomy with Histologic Correlation, vol. 3 No. 3, May/Jun. 1993.

Bromm et al., Human Neurobiology: Nerve Fibre Discharges, Cerebral Potentials and Sensations Induced by CO2 laser Stimulation, vol.3, (1984) pp. 33–40.

Kolarik et al., Photonucleolysis of Intervertebral Disc and it's Herniation, vol. 51, (1990) pp. 69–71.

Vorwerck et al., Laserablation des Nucleus Pulposus: Optische Eigenschaften von Degeneriertem Bandscheibengewebe im Wellenlangenbereich von 200 bis 2200nm, vol. 151 No. 6 (1989) pp. 725–728.

Wolgin et al., Excimer Ablation of Human Intervertebral Disc at 308 Nanometers, vol. 9, (1989) pp. 124–131.

Davis, Early experience with Laser Disc Decompression, vol. 79 No. 1, (1992) j. Florida M.A..

Quigley et al., Laser Discectomy: Comparision of Systems, vol. 19 No. 3 (1994) pp. 319–322.

Mehta et al., The Treatment of Chronic back Pain: A Preliminary survey of the Effects of Radiofrequency Denervation of the Posterior Vertebral Joints, vol. 34 (1979) pp. 768–775.

Patil et al, Percutaneous Discectomy Using the Electomagnetc Field Focusing Probe: A Feasabilty Study.

McCulloch et al., CMA Journal: Percutaneous Radiofrequency Lumbar Rhizolysis (rhizotomy), vol. 116, Jan. 8, 1977.

Yonezawa et al., The System and Procedure of Percutaneous Intradiscal Laser Nucleotomy, vol. 15 No. 11 (1990).

Siminia et al., Effects of 434 MHz Microwave Hyperthermia applied to the rat in the region of the cervical Spinal Cord, vol. 3 No. 5 (1987) pp. 441–452.

Sluijter et al., Treatment of Chronic Back and Neck Pain by Percutaneous Therman Lesions, vol. 3 (1981.

Christian, C. et al., "Allograft Anterior Cruciate Ligament Reconstruction with Patellar Tendon: An Endoscopic Technique"*Operative Techniques in Sports Medicine*, vol. 1, No. 1, Jan. 1993, pp. 50–57.

Houpt, J. et al., "Experimental Study of Temperature Distributions and Thermal Transport During Radiofrequency Current Therapy of the Intervertebral Disc", *SPINE*, vol. 21, No. 15, (1996), pp. 1808–1813.

Troussier, B. et al., "Percutaneous Intradiscal Radio–Frequency Thermocoagulation: A Cadaveric Study", *SPINE*, vol. 20, No. 15 (Aug. 1995), pp. 1713–1718.

Beading, L., "Bi–Polar electrosurgical devices: Sculpting the future of arthroscopy", *Orthopedics today*, vol. 17, No. 1, Jan. 1997, 4 pages.

Ellman International Mfg., Inc., 1989, Catalog, pp. 1–15, 20.

Cosset, J.M., Resistive Radiofrequency (Low Frequency) Interstitial Heating (RF Technique), Interstitial Hyperthermia, Dec. 6, 1993, pp. 3–5, 37.

Attachment I: Competitive Literature on Generators with Bipolar Capabilities, IME Co., Ltd., pp. 60–86.

Attachment II: Competitive Literature on Bipolar Forceps and Footswitch Controls, IME Co., Ltd. pp. 87–104.

* cited by examiner

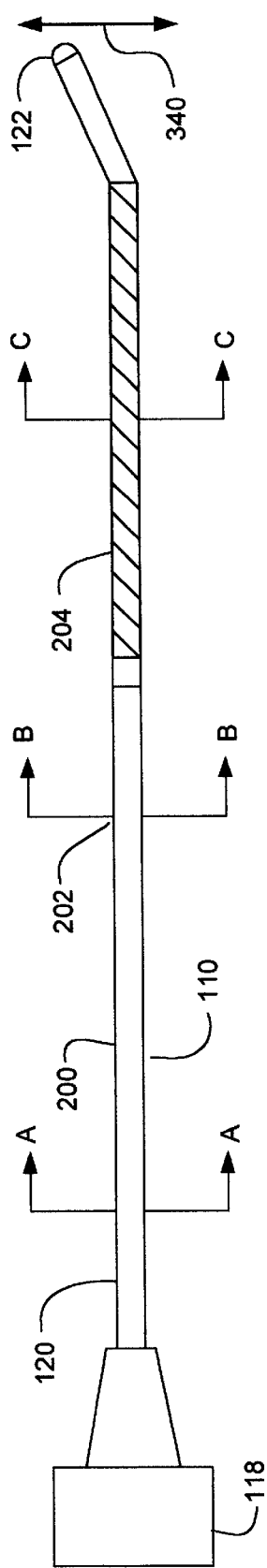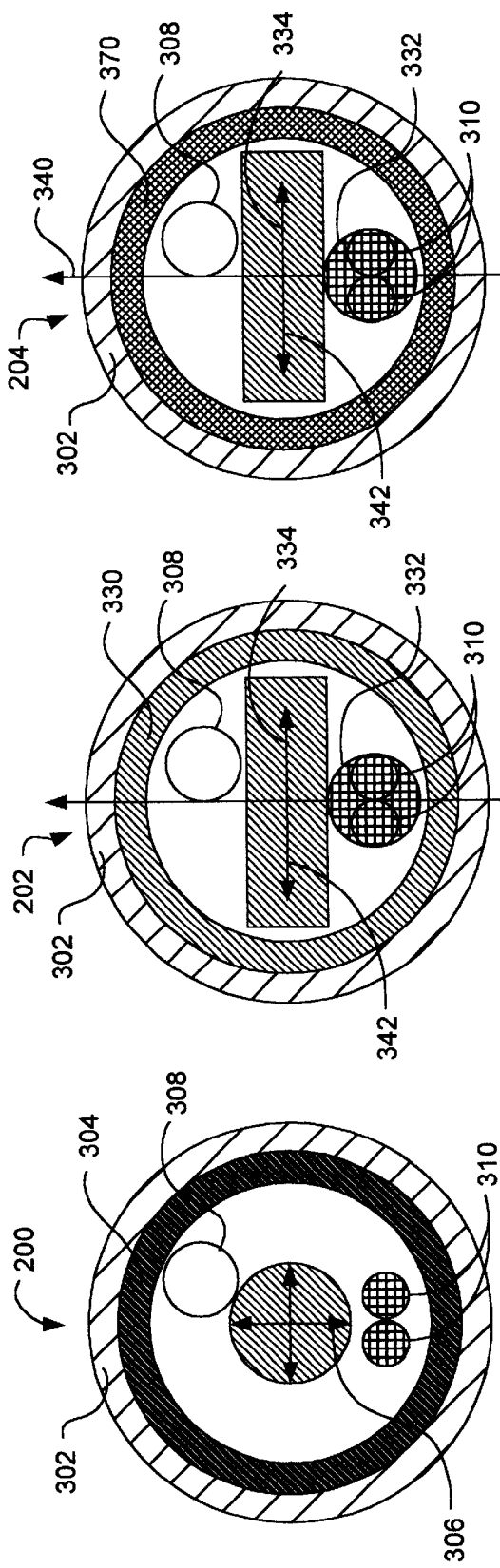
FIG. 2
FIG. 3A  A-A
FIG. 3B  B-B
FIG. 3C  C-C

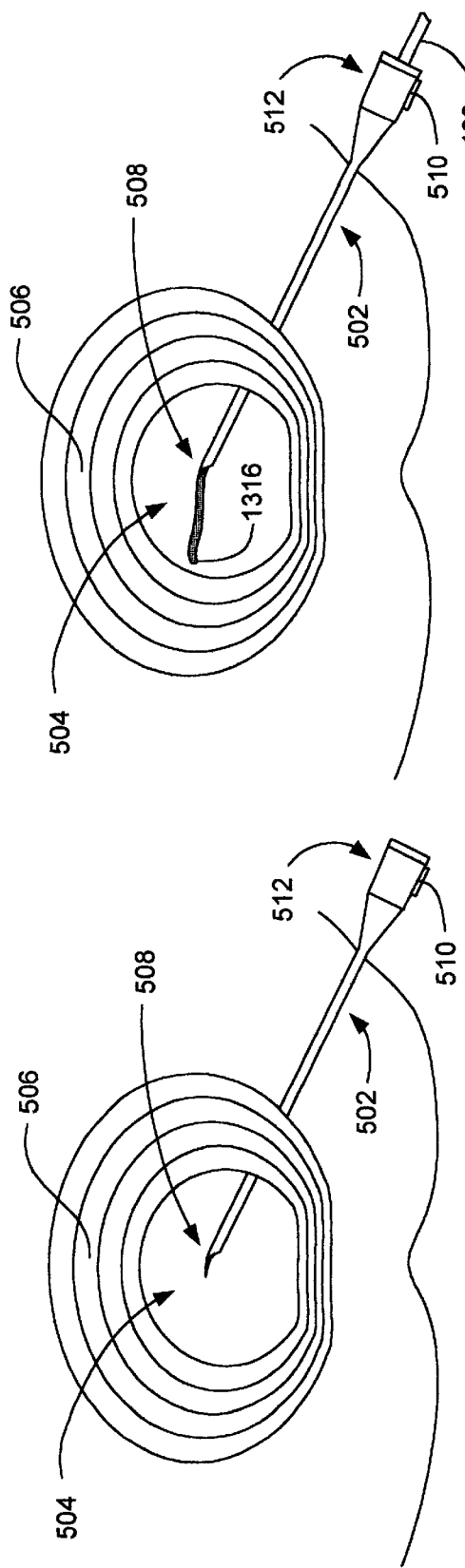
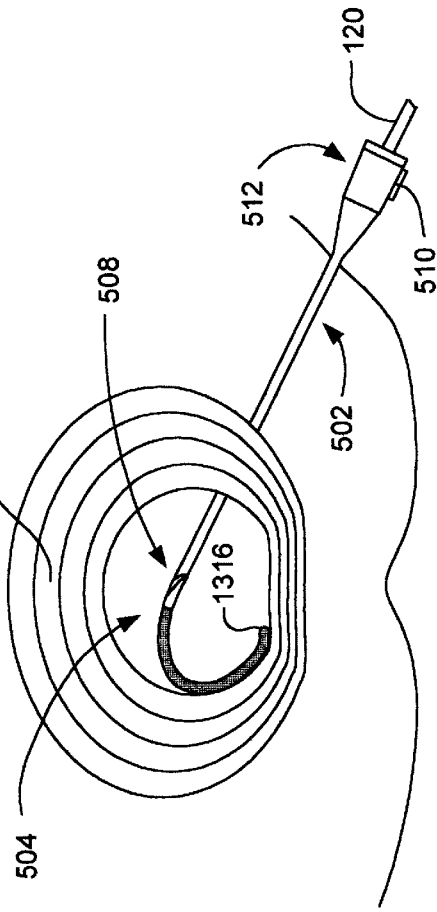
FIG. 5A
FIG. 5B
FIG. 5C

APPARATUS FOR DELIVERY OF ENERGY TO A SURGICAL SITE

This application is a continuation-in-part of: PCT/US97/19189, filed Oct. 22, 1997, entitled Method and Apparatus For Treating Intervertebral Discs, which is a continuation-in-part of U.S. application Ser. No. 60/029,735, entitled "Method and Apparatus for Treating Intervertebral Discs," filed Oct. 23, 1996, now abandoned; U.S. application Ser. No. 60/029,600, entitled "Method and Apparatus for Treating Intervertebral Discs," filed Oct. 23, 1996, now abandoned; U.S. application Ser. No. 60/029,734, entitled "Method and Apparatus for Treating Intervertebral Discs," filed Oct. 23, 1996, U.S. application Ser. No. 60/029,602, entitled "Method and Apparatus for Treating Intervertebral Discs," filed Oct. 23, 1996, now abandoned; U.S. application Ser. No. 60/046,002, entitled "Method and Apparatus for Treating Intervertebral Discs with Radio Frequency Heating," filed May 8, 1997, now abandoned; U.S. application Ser. No. 60/046,001, entitled "Method and Apparatus for Treating Intervertebral Discs with Resistive Heating," filed May 8, 1997, now abandoned; U.S. application Ser. No. 60/047,820, entitled "Method and Apparatus for Treating Intervertebral Discs with Electromagnetic Energy," filed May 28, 1997, now pending; U.S. application Ser. No. 60/047,681, entitled "Method and Apparatus for Treating Intervertebral Discs with Thermal Energy," filed May 28, 1997, now pending; U.S. application Ser. No. 60/045,941, entitled "Method and Apparatus for Delivering or Removing Material from the Interior of an Intervertebral Disc," filed May 8, 1997, now abandoned; U.S. application Ser. No. 60/047,818, entitled "Method and Apparatus for Treating Annular Fissures in Intervertebral Discs," filed May 28, 1997, now pending; U.S. application Ser. No. 60/047,848, entitled "Method and Apparatus for Treating Intervertebral Disc Degeneration," filed May 28, 1997, now pending; U.S. application Ser. No. 08/881,525, entitled "Method and Apparatus for Treating Intervertebral Discs with Thermal Energy," filed Jun. 24, 1997, now U.S. Pat. No. 6,122,549; U.S. application Ser. No. 08/881,692, entitled "Method and Apparatus for Treating Intervertebral Discs with Electromagnetic Energy," filed Jun. 24, 1997, now U.S. Pat. No. 6,073,051; U.S. application Ser. No. 08/881,527, entitled "Method and Apparatus for Delivering or Removing Material from the Interior of an Intervertebral Disc," filed Jun. 24, 1997, now U.S. Pat. No. 5,980,504; U.S. application Ser. No. 08/881,693, entitled "Method and Apparatus for Treating Annular Fissures in Intervertebral Discs," filed Jun. 24, 1997, now U.S. Pat. No. 6,007,570; and U.S. application Ser. No. 08/881,694, entitled "Method and Apparatus for Treating Intervertebral Disc Degeneration," filed Jun. 24, 1997, now U.S. Pat. No. 6,095,149. This application is a continuation of application Ser. No. 08/547,510, filed Oct. 24, 1995, now U.S. Pat. No. 5,785,705 enitled RF Method For Controlled Depth Ablation of Soft Tissue, application Ser. No. 08/637,095, filed Apr. 24, 1996, entitled Method And Apparatus For Controlled Contraction of Soft Tissue, application Ser. No. 08/696,051, filed Aug. 13, 1996, entitled In VIVO Formed Thermally Contracted Collagen Tissue, application Ser. No. 08/714,987, filed Sep. 17, 1996, entitled Method And Apparatus For Controlled Contraction of Soft Tissue, application Ser. No. 08/888,359, filed Jul. 3, 1997, entitled Orthopedic Apparatus For Controlled Contraction of Collagen Tissue, are all incorporated herein by reference in their entirety.

FIELD OF THE INVENTION

This invention relates generally to an apparatus for delivery of energy to a surgical site and more particularly to an apparatus which can provide a band of energy to the surgical site.

DESCRIPTION OF THE RELATED ART

Instability of peripheral joints has long been recognized as a significant cause of disability and functional limitation in patients who are active in their daily activities, work or sports. Diarthrodial joints of the musculoskeletal system have varying degrees of intrinsic stability based on joint geometry and ligament and soft tissue investment. Diarthrodial joints are comprised of the articulation of the ends of bones and their covering of hyaline cartilage surrounded by a soft tissue joint capsule that maintains the constant contact of the cartilage surfaces. This joint capsule also maintains, within the joint, the synovial fluid that provides nutrition and lubrication of the joint surfaces. Ligaments are soft tissue condensations in or around the joint capsule that reinforce and hold the joint together while also controlling and restricting various movements of the joints. Ligaments, joint capsules, and connective tissue are largely comprised of collagen.

When a joint becomes unstable, its soft tissue or bony structures allow for excessive motion of the joint surfaces relative to each other, and in direction not normally permitted by the ligaments or capsule. When one surface of a joint slides out of position relative to the other surface, but some contact remains, subluxation occurs. When one surface of the joint completely disengages and losses contact with the opposing surface, a dislocation occurs. Typically, the more motion a joint normally demonstrates, the more inherently loose the soft tissue investment is surrounding the joint. This makes some joints more prone to instability than others. The shoulder, glenohumeral joint, for example, has the greatest range of motion of all peripheral joints. It has long been recognized as having the highest subluxation and dislocation rate because of its inherent laxity relative to more constrained "ball and socket" joints such as the hip.

Instability of the shoulder can occur congenitally, developmentally, or traumatically and often becomes recurrent, necessitating surgical repair. In fact, subluxations and dislocations are a common occurrence and cause for a large number of orthopedic procedures each year. Symptoms include pain, instability, weakness and limitation of function. If the instability is severe and recurrent, functional incapacity and arthritis may result. Surgical attempts are directed toward tightening the soft tissue restraints that have become pathologically loose. These procedures are typically performed through open surgical approaches that often require hospitalization and prolonged rehabilitation programs.

More recently, endoscope (arthroscopic) techniques for achieving these same goals have been explored with variable success. Endoscopic techniques have the advantage of being performed through smaller incisions, and therefor are usually less painful. Such techniques are performed on an outpatient basis, associated with less blood loss and lower risk of infection and have a more cosmetically acceptable scar. Recovery is often faster postoperatively than using open techniques. However, it is often more technically demanding to advance and tighten capsule or ligamentous tissue arthroscopically because of the difficult access to pathologically loose tissue, and because it is very hard to determine how much tightening or advancement of the lax tissue is clinically necessary. In addition, fixation of advanced or tightened soft tissue is more difficult arthroscopically than through open surgical methods.

Collagen connective tissue is ubiquitous in the human body and demonstrates several unique characteristics not found in other tissues. It provides the cohesiveness of the musculoskeletal system, the structural integrity of the viscera as well as the elasticity of integument. There are basically five types of collagen molecules, with Type I being most common in bone, tendon, skin and other connective tissues, and Type III is common in muscular and elastic tissues.

Intermolecular cross links provide collagen connective tissue with unique physical properties of high tensile strength and substantial elasticity. A previously recognized property of collagen is hydrothermal shrinkage of collagen fibers when elevated in temperature. This unique molecular response to temperature elevation is the result of rupture of the collagen stabilizing cross links and immediate contraction of the collagen fibers to about one-third of their original lineal distention. Additionally, the caliber of the individual fibers increases greatly, over four fold, without changing the structural integrity of the connective tissue.

There has been discussion in the existing literature regarding alteration of collagen connective tissue in different parts of the body. One known technique for effective use of this knowledge of the properties of collagen is through the use of infrared laser energy to effect tissue heating. The importance in controlling the localization, timing and intensity of laser energy delivery is recognized as paramount in providing the desired soft tissue shrinkage effects without creating excessive damage to the surrounding non-target tissues.

Shrinkage of collagen tissue is important in many applications. One application is the shoulder capsule. The capsule of the shoulder consists of a synovial lining and three well defined layers of collagen. The fibers of the inner and outer layers extend in a coronal access from the glenoid to the humerus. The middle layer of the collagen extends in a sagittal direction, crossing the fibers of the other two layers. The relative thickness and degree of intermingling of collagen fibers of the three layers vary with different portions of the capsule. The ligamentous components of the capsule are represented by abrupt thickenings of the inner layer with a significant increase in well organized coarse collagen bundles in the coronal plane.

The capsule functions as a hammock-like sling to support the humeral head. In pathologic states of recurrent traumatic or developmental instability this capsule or pouch becomes attenuated, and the capsule capacity increases secondary to capsule redundance. In cases of congenital or developmental multi-directional laxity, an altered ratio of Type I to Type III collagen fibers may be noted. In these shoulder capsules, a higher ratio of more elastic type III collagen has been described.

There exists a need for an apparatus to effect controlled ablation of soft tissue along a painted band or line created by the introduction of energy. It would be desirable to provide an ablation apparatus which can provide controlled ablation depth of soft tissue to shrink the tissue to a desired state along a selectable surface, including but not limited to a narrow line.

SUMMARY OF THE INVENTION

It is an object of the present invention to provide a surgical apparatus which creates controlled delivery of energy to a desired tissue site.

Another object of the present invention is to provide a surgical apparatus which can paint a band or line of ablation along a selected tissue site.

A further object of the present invention is to provide a surgical apparatus which provides selectable painting ablation of a tissue site.

Yet another object of the present invention is to provide a surgical apparatus which provides continuous and controllable, adjustable ablation of soft tissue.

A further object of the present invention is to provide a surgical apparatus which provides for the maximum amount of collagen contraction without dissociation of the collagen structure.

Yet another object of the present invention is to provide a surgical apparatus to deliver a controlled amount of energy to tissue site in order to contract and restrict the soft tissue elasticity and improve joint stability.

These and other objects of the invention can be obtained with an apparatus for delivering energy to a surgical site from an energy source. The apparatus includes; a handle, an actuator, a shaft, and a deflection wire. The actuator is movably coupled to the handle. The actuator moves from a first position to a second position. The shaft includes a proximal end, a deflectable portion and an energy delivery portion. The proximal end of the shaft is coupled to the handle. The energy delivery portion is coupled to the energy source to deliver energy to the surgical site. The deflection wire includes a proximal portion and a distal portion. The distal portion is affixed to the shaft. The proximal portion is affixed to the actuator. A movement of the actuator from the first position to the second position moves the deflection wire to produce a deflection of the deflectable portion.

In an alternate embodiment of the invention an apparatus for delivering energy to a surgical site from an energy source is provided. The apparatus includes; a handle, an actuator, a shaft, a deflection wire, a sensor and a feedback control module. The actuator is movably coupled to the handle. The actuator moves from a first position to a second position. The shaft includes a proximal end, a deflectable portion and an energy delivery portion. The proximal end of the shaft is coupled to the handle. The energy delivery portion is coupled to the energy source to deliver energy to the surgical site. The deflection wire includes a proximal portion and a distal portion. The distal portion is affixed to the shaft. The proximal portion is affixed to the actuator. A movement of the actuator from the first position to the second position moves the deflection wire to produce a deflection of the deflectable portion. The sensor is positioned adjacent the energy delivery portion of the shaft to provide a signal indicating an amount of energy delivered from the energy source to surgical site. The feedback control module is coupled to the sensor and to the energy source. The feedback control module includes a logic responsive to the signal for adjusting a level of energy delivered from the energy source to the energy delivery portion of the shaft.

DESCRIPTION OF THE DRAWINGS

FIG. 2 illustrates a shaft for use with a surgical apparatus according to the present invention.

FIGS. 3A–C show various cross-sectional views of the shaft shown in FIG. 2.

FIGS. 5A–C illustrate a spinal disc pierced by a cannula through which a shaft of a surgical apparatus is introduced.

DETAILED DESCRIPTION OF THE PREFERRED EMBODIMENTS

Figure 1A:
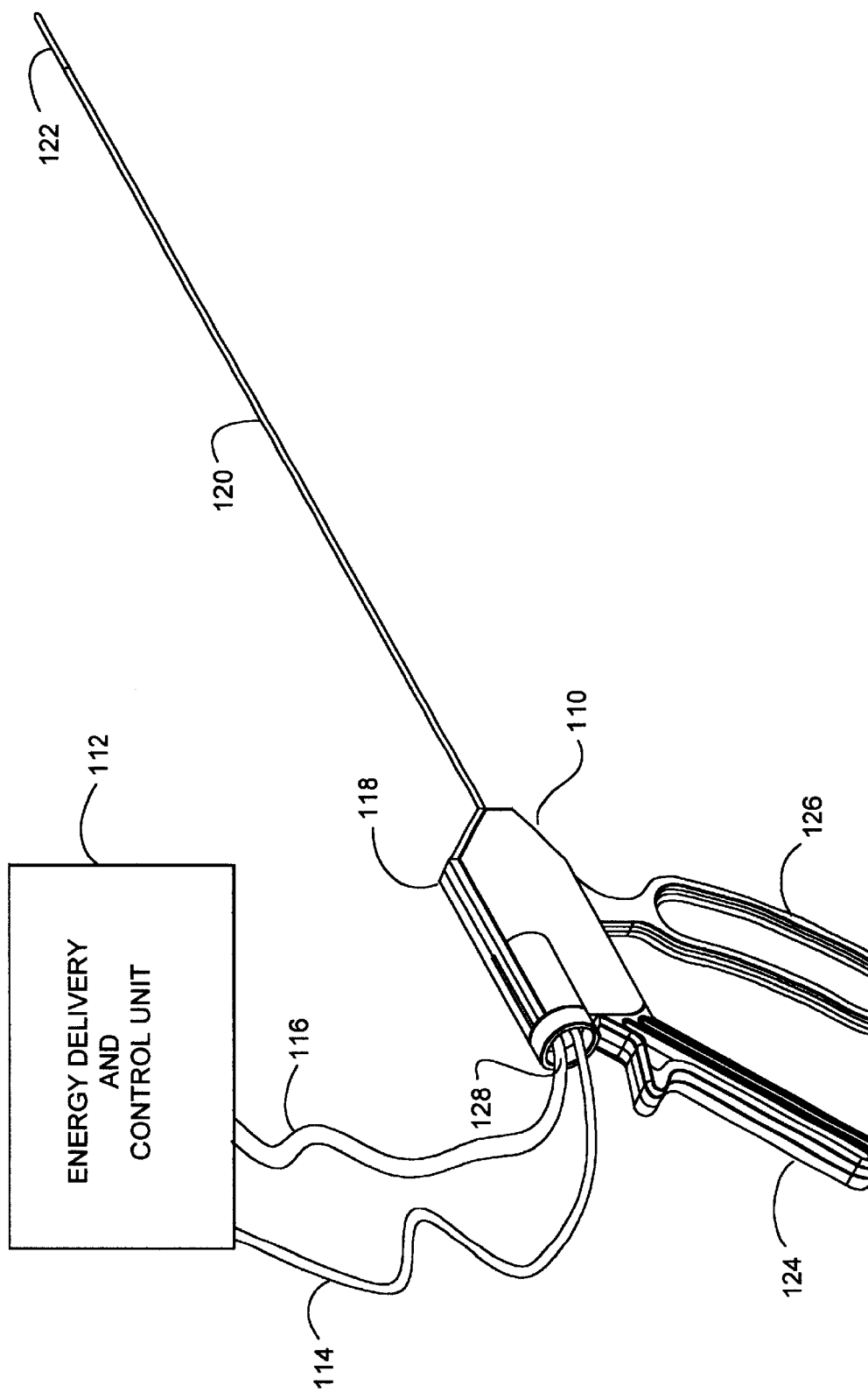
FIGS. 1A–B is an isometric view of a surgical apparatus.

FIG. 1A illustrates an energy delivery system according to the present invention. The system includes a surgical apparatus 110, an energy delivery and control unit 112, an energy supply cord 114 and a sensor signal cord 116. The surgical apparatus 110 includes a handle 118 and a shaft 120 with a tip 122. The handle 118 includes a stationary handle 124, an actuator 126 and a utility port 128.

The utility port 128 is coupled with the energy supply cord 114 and the sensor signal cord 116. The energy supply cord 114 and the sensor signal cord 116 are in turn coupled with the energy delivery and control unit 112. The actuator 126 is pivotally coupled with the stationary handle 124 such that the actuator 126 can be moved relative to the stationary handle 124.

Figure 1B:
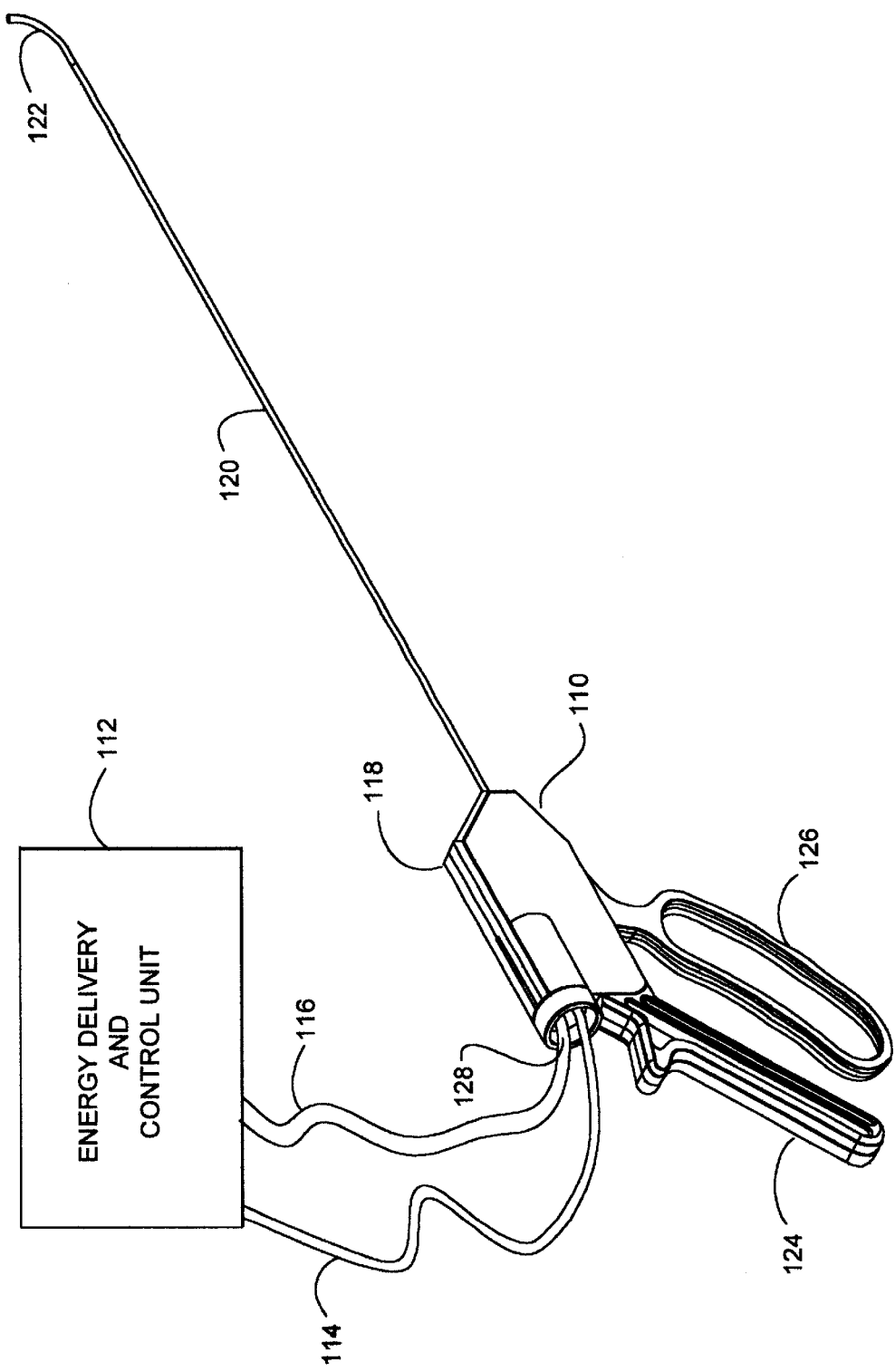

In operation, the shaft tip 122 can be deflected by pulling the actuator 126 toward the stationary handle 124 as illustrated in FIG. 1B. Energy is supplied from the energy delivery and control unit 112 to the surgical apparatus 110 via the energy supply cord 114. The energy delivery and control unit 112 receives a signal from a sensor (not shown) via the sensor signal cord 116. In an embodiment of the invention, the sensor is positioned at the tip 122 adjacent an energy delivery portion. The energy delivery and control unit 112 adjusts the amount of energy delivered from the energy delivery and control unit 112 in response to the signal received from the sensor.

FIG. 2 is a detailed diagram of the shaft 120 illustrated in FIG. 1A. The shaft 120 is divided into a proximal section 200, a transition section 202 and an energy delivery section 204. Suitable lengths for the energy delivery section 204 include, but are not limited to, two inches long starting from the tip.

FIGS. 3A–C provide cross-sectional views of the proximal section 200, transition section 202 and energy delivery section 204 illustrated in FIG. 2. FIG. 3A illustrates the proximal section 200 of the shaft 120. This view is taken along lines A—A illustrated in FIG. 2. The proximal section 200 includes an outer polyamide sheath 302, a stainless steel tube 304, a stainless steel core 306, a deflection wire 308, and sensor and energy delivery wires 310. The proximal section has no preferred bending axis since its moment of inertia is determined primarily by the rigid stainless steel tube 304 and the core member 306. Thus, the proximal section of the shaft 120 resists both bending and buckling.

FIG. 3B illustrates the transition section 202 of the shaft 120. This view is taken along lines B—B illustrated in FIG. 2. The stainless steel tube 304 found in FIG. 3A has been replaced with a relatively flexible polyamide tube 330. The polyamide tube 330 is housed within the outer polyamide sheath 302. Both of these tubes are flexible. The stainless steel core has transitioned to a cross member 334. The cross member 334 has a preferred bending axis 340 which is orthogonal to the longitudinal axis 342 of the stainless steel cross-member 334. This cross-member 334 provides the needed resistance to deflection along axis 342 while allowing deflection along axis 340.

FIG. 3C illustrates the energy delivery section 204 of the shaft 120. This view is taken along lines C—C illustrated in FIG. 2. Outer polyamide sheath 302 wraps around an energy delivery device 370. In the interior of the shaft 120 stainless steel cross-member 334 provides the needed resistance to deflection along axis 342. In FIGS. 3B and 3C, the sensor and energy delivery wires 310 include a coating 332 for insulating the sensor and energy delivery wires 310 from the energy delivered to the energy delivery device 370.

In FIGS. 3A–C, the sensor and energy delivery wires 310 extend from the shaft 120 to the utility port 128. The wires are coupled at the utility port to the energy delivery device 370 to allow energy to be delivered to the energy delivery portion 370 of the shaft, and to allow feedback from a sensor in the energy delivery portion to be used to regulate the level of energy delivered by the energy delivery and control unit 112.

Suitable energy delivery devices include, but are not limited to, resistive heaters, monopolar RF electrode and bipolar RF electrodes. Suitable locations for the sensor include, but are not limited to, the inside of stainless steel tube 304, inside of the flexible polyamide tube 330 and/or at the tip 122. Suitable sensors include, but are not limited to, impedance sensors and temperature sensors such as thermocouples.

In operation bending along axis 340 is brought about by drawing the deflection wire 308 proximally. The deflection wire 308 is fastened to the distal portion of cross-member 334 but is otherwise free to move longitudinally along the inside of shaft 120. Drawing deflection wire 308 proximally causes compressional forces on cross-member 334. Cross-member 334 bends along axis 340 in response to the compression. The bend of cross-member 334 causes deflection of the tip 122 as illustrated in FIG. 1B.

Figure 4A:
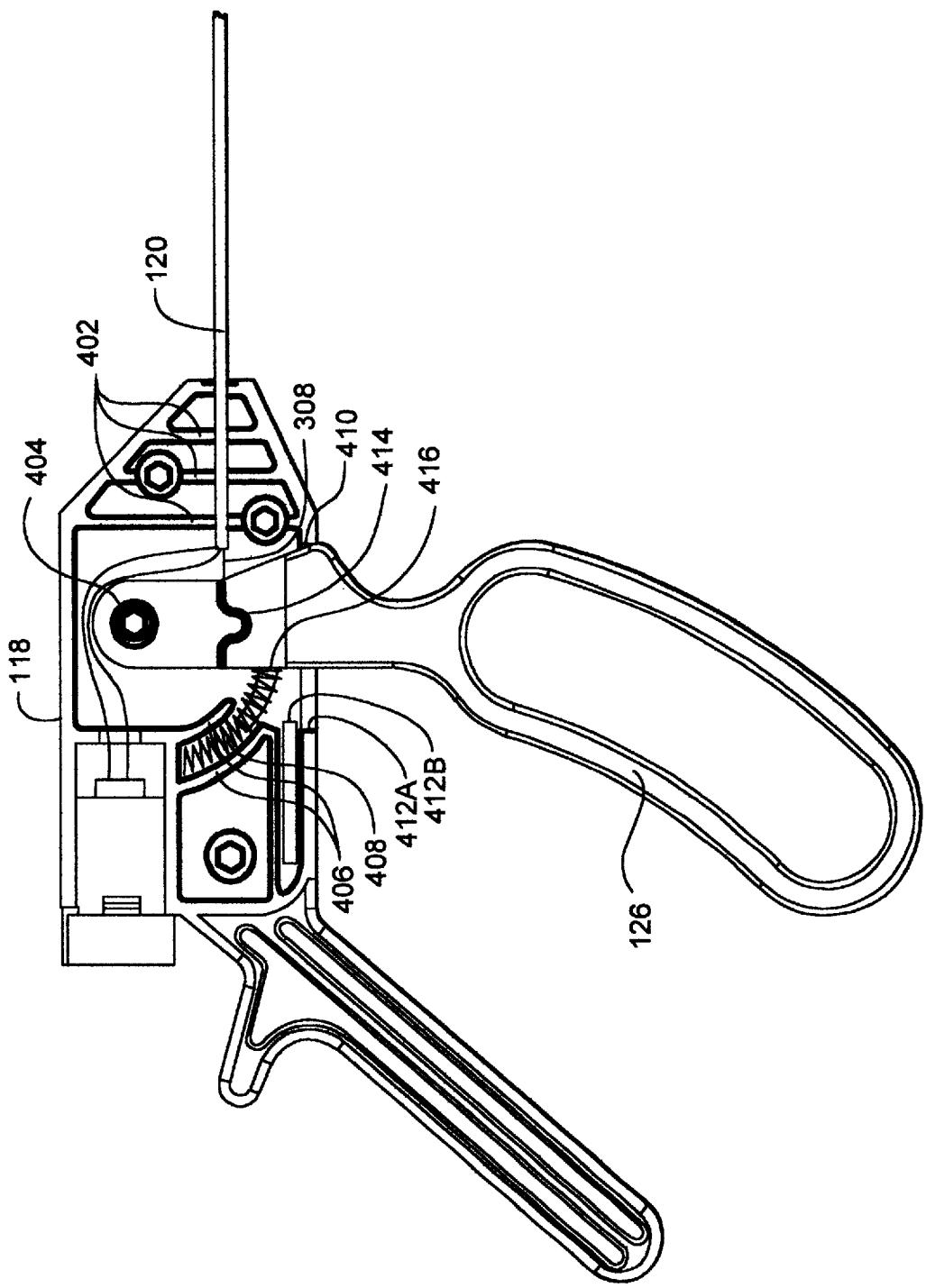
FIG. 4A–B are cross sectional views of the handle portion of a surgical apparatus.

FIG. 4A is a cross section of the handle 118. The handle 118 includes a shaft seat 402, a pivot structure 404, a spring seat 406, a spring 408, a forward stop 410 and a rearward stop 412A. The actuator 126 includes an arcuate groove 414, a grip and a biasing support 416.

The actuator 126 is pivotally coupled with the pivot structure 404 by positioning an aperture in the actuator 126 over the pivot structure 404. The actuator 126 can be pivoted about the pivot structure 404 from a first position to a second position.

The spring 408 is seated within the spring seat 406 so as to apply pressure to the biasing support 416 of the actuator 126. The pressure of the spring 408 on the biasing support biases the actuator toward a forward position where the actuator contacts the forward stop 410.

The shaft 120 is seated in the shaft seat 402. The deflection wire 308 exits the shaft 120. The distal end of the deflection wire 308 includes a resilient arcuate portion positioned within the arcuate groove 414, to affix the wire to the actuator.

Figure 4B:
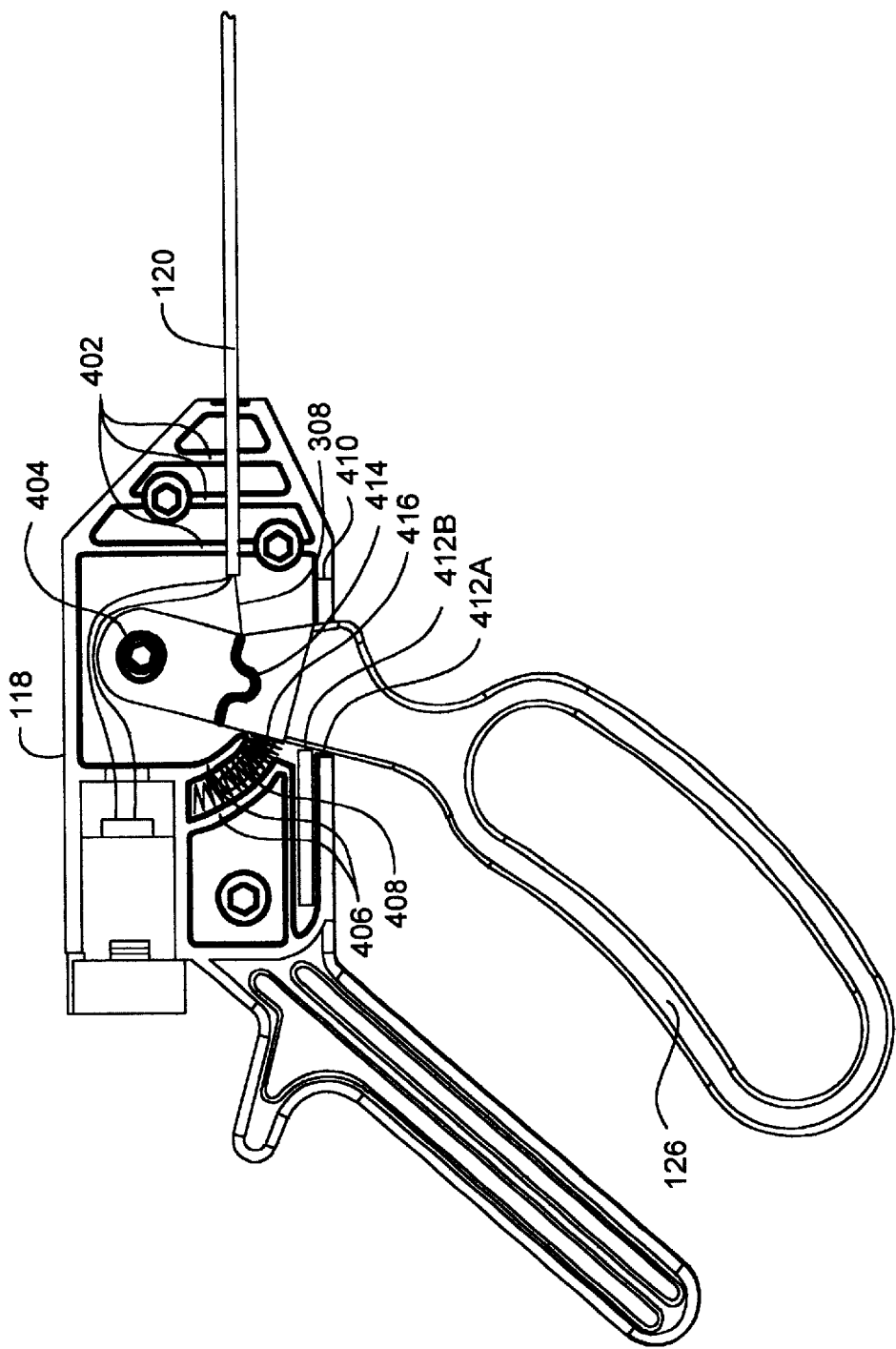

In operation, the actuator 126 is pulled toward the stationary handle 124 as illustrated in FIG. 4B. The movement of the actuator 126 causes the arcuate groove 414 to be pulled rearward. Since the deflection wire 308 is fixed within the arcuate groove 414, the deflection wire 308 is also pulled rearward. The proximal motion of the deflection wire causes the tip 122 to become deflected as illustrated in FIG. 1B. An increased degree of proximal motion of the deflection wire causes an increased deflection of the tip. The motion of the actuator can be limited by the rear stop 412A in order to prevent damage resulting from over deflection. The rearward stop 412A can include an adjustable pin 412B which can be used to set the degree of deflection.

The surgical apparatus 110 is suitable for use in numerous tissues sites within a body. Suitable tissue sites include, but are not limited to, a nucleus pulposus of a spinal disk. FIGS. 5A–C illustrate use of the surgical apparatus 110 to deliver energy to the nucleus pulposus 504 of a spinal disc 506. In FIG. 5A a cannula/introducer 502 is introduced through a patient's back along a path which intercepts a selected disc 506. The insertion of the cannula 502 into the appropriate location may be accomplished with x-ray imaging which allows visualization of the cannula tip 508 with respect to the selected spinal disc 506. The cannula tip 508 pierces the spinal disc 506 and extends a desired distance into the nucleus pulposus 504. A visual indicator 510 on hub 512 of the cannula 502 shows the orientation of the opening in the cannula tip 508.

In FIG. 5B the shaft 120 is inserted through the hub 512 of the cannula 502. The surgical apparatus 110 can include depth markings on the shaft 120 to indicate the point at which the tip 122 and energy delivery section 204 of the shaft 120 has reached the nucleus pulposus 504.

In FIG. 5C the continued insertion of the shaft 120 causes the tip 122 to traverse the interior walls of the annulus fibrosus. The tip 122 is then deflected to an angle which approximates the curvature of the inside of the disc 506. This deflection allows an increased portion of the shaft 120 to be contacted with the inside of the disc 506. In this orientation energy can be delivered to a specific tissue site, i.e. a fissure or rupture. The deflection of the tip 122 the motion of the actuator 126 from the forward to the reverse positions shown in FIGS. 4A–B can also be used to aid in steering the tip 122 to a particular tissue site within the body.

Figure 6:
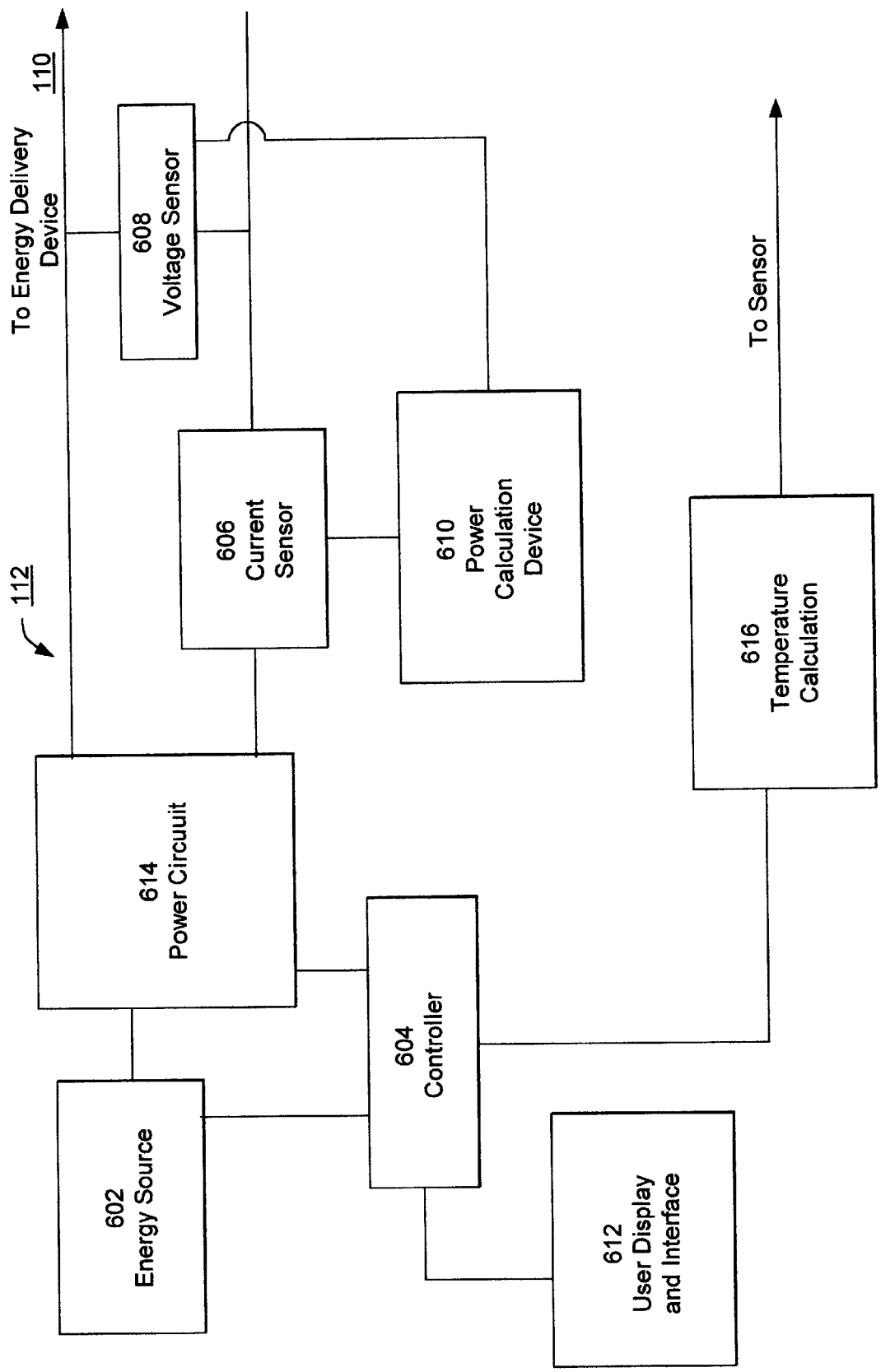
FIG. 6 is a block diagram of an energy delivery and control unit.
Figure 7:
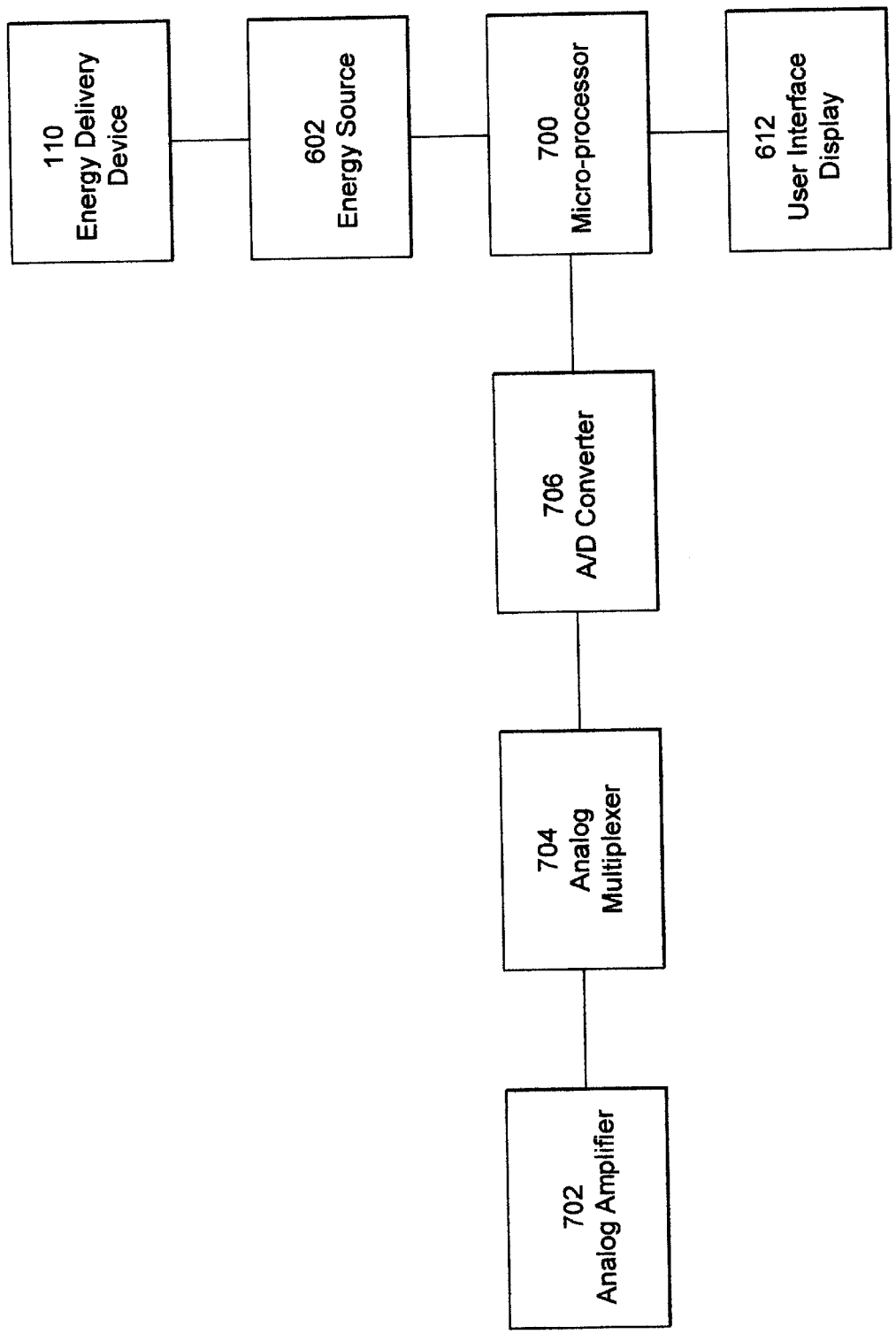
FIG. 7 is a block diagram of an embodiment illustrating an analog amplifier, analog multiplexer and microprocessor used with the energy delivery and control unit of FIG. 6.

FIGS. 6–7 illustrate one embodiment of the energy delivery and control unit 112. The illustrated energy delivery and control unit 112 is used with a thermocouple as the sensor, a resistive heating element as the energy delivery device and an electrical energy source as the energy source. The embodiment illustrated in FIGS. 6 and 7 are readily adaptable to other energy sources, sensors and energy delivery devices. Suitable energy sources include, but are not limited to, RF energy sources and thermal energy sources.

The energy delivery control unit 112 includes an energy source 602, a controller 604 with a microprocessor, a current sensor 606, a voltage sensor 608, a power calculator 610, a user display interface 612, a power circuit 614 and a temperature calculator 616.

When the surgical apparatus 110 is positioned at a tissue site, a signal indicating the temperature of the tissue site is provided by a thermocouple sensor. The signal from the thermocouple sensor is provided to the temperature calculator. The signal from the temperature calculator is provided to the controller 604.

The resistive heating element within the surgical apparatus 110 is in energy communication with the energy source 602. The current delivered through the resistive heating element is passed through the current sensor 606. The voltage of the delivered current can be measured by the voltage sensor 608. The output of the current sensor 606 and voltage sensor 668 are provided to a power calculation device 610. The output from the power calculation device 610 is provided to the controller 604.

In operation, the controller 604 monitors the output from the temperature calculator 616 and the power calculation device 610. The controller 604 can display these values at the user display and interface 612. When controller 604 detects that the temperature falls outside a desired range, the controller 604 provides an output to the power circuit 614. The output to the power circuit 614 is used to adjust the level of energy delivered from the energy source 602. For instance, when the temperature at the temperature site is below the desired temperature range, the output from the controller causes the power circuit 614 to increase the amount of energy delivered from the energy source 602. The degree of energy level change is a function of the amount of power energy being delivered from the energy source 602 as indicated by the power calculation device 610.

Controller 604 can be a digital or analog controller or a computer with software. When controller 604 is a computer, it can include a CPU coupled through a system bus. Included in this system can be a keyboard, a disc drive or other nonvolatile memory system, a display, and other peripherals, as are known in the art. Also coupled to the bus can be a program memory and a data memory.

User interface and display 612 includes operator controls and a display. Controller 604 can be coupled to imaging systems well known in the art.

The output of current sensor 606 and voltage sensor 608 can be used by controller 604 to maintain a selected power level at resistive heating elements. A predetermined profile of power, temperature or energy to be delivered can be incorporated in controller 604.

Circuitry, software, and feedback to controller 604 result in process control and in the maintenance of the selected power that is independent of changes in voltage or current. Control can include (i) the selected power and (ii) the duty cycle (wattage and on-off times). These process variables are controlled and varied while maintaining the desired delivery of power independent of changes in voltage or current, based on temperatures monitored at the thermocouple.

In the embodiment illustrated in FIG. 7, current sensor 606 and voltage sensor 608 are connected to the input of an analog amplifier 702. Analog amplifier 702 can be a conventional differential amplifier circuit for use with a sensor. The output of analog amplifier 702 is sequentially connected by an analog multiplexer 704 to the input of A/D converter 706. The output of analog amplifier 702 is a voltage which represents the respective sensed parameters. Digitized amplifier output voltages are supplied by A/D converter 706 to microprocessor 700. Microprocessor 700 may be a type 68HCII available from Motorola. However, it will be appreciated that any suitable microprocessor or general purpose digital or analog computer can be used for the parameters of temperature, voltage or current.

Microprocessor 700 sequentially receives and stores digital representations of temperature. Each digital value received by microprocessor 700 corresponds to different parameters.

Calculated power and temperature values can be indicated on user interface and display 612. Alternatively, or in addition to the numerical indication of power, calculated power values can be compared by microprocessor 700 with power limits. When the values exceed predetermined power or temperature values, a warning can be given on user interface and display 612, and additionally, the delivery of electromagnetic energy can be reduced, modified or interrupted. A control signal from microprocessor 700 can modify the power level supplied by energy source 602.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications, as are suited to the particular use contemplated. It is intended that the scope of the invention be defined by the following claims and their equivalents.

What is claimed is:

1. An apparatus for delivering energy to a surgical site from an energy source, comprising:

a handle;

an actuator movably coupled to the handle with a pivot structure to arcuately move from a first position to a second position;

a shaft including a proximal end, a deflectable portion and an energy delivery portion, and the proximal end of the shaft coupled to the handle and the energy delivery portion coupled to the energy source for delivery of energy to the surgical site; and a deflection wire including a proximal portion and a distal portion, and the distal portion fixed to the shaft, and the proximal portion affixed to the actuator, and a movement of the actuator from the first position to the second position moving the deflection wire to produce a deflection of the deflectable portion, wherein an axis of rotation defined by the pivot structure is substantially perpendicular to a plane defined by the proximal portion of the deflection wire.

2. The apparatus of claim 1, wherein the actuator further comprises:

a pivot point located substantially at an end of the actuator;

a grip positioned at an opposing end of the actuator; and a fastener positioned between the grip and the pivot point, and the deflection wire fastened to the fastener.

3. The apparatus of claim 2, wherein the fastener portion comprises an arcuate groove defined between opposing surfaces of said actuator; and wherein the deflection wire further comprises;

an arcuate portion located at the proximal portion of the deflection wire, and the arcuate portion positioned within the arcuate groove.

4. An apparatus for delivering energy to a surgical site from an energy source, comprising:

a handle;

an actuator movably coupled to the handle to move from a first position to a second position;

a shaft including a proximal end, a deflectable portion and an energy delivery portion, and the proximal end of the shaft coupled to the handle and the energy delivery portion coupled to the energy source for delivery of energy to the surgical site;

a deflection wire including a proximal portion and a distal portion, and the distal portion fixed to the shaft, and the proximal portion affixed to the actuator, and a movement of the actuator from the first position to the second position moving the deflection wire to produce a deflection of the deflectable portion;

a sensor positioned adjacent the energy delivery portion of the shaft to provide a signal indicating an amount of energy delivered from the energy source to surgical site; and a feedback control module coupled to the sensor and to the energy source, and the feedback control module including a logic responsive to the signal for adjusting a level of energy delivered from the energy source to the energy delivery portion of the shaft.

5. The apparatus of claim 2, wherein the actuator further comprises a biasing support.

6. The apparatus of claim 2, wherein the handle further comprises a spring seat and a spring seated within said spring seat.

7. The apparatus of claim 1, wherein the energy source is a electrical energy source.

8. The apparatus of claim 1, wherein the energy source is an RF energy source.

9. The apparatus of claim 1, wherein the energy delivery portion includes a resistive heating element.

10. The apparatus of claim 1, wherein the energy delivery portion includes a monopoly RF electrode.

11. The apparatus of claim 1, wherein the energy delivery portion includes a bipolar RF electrode.

* * * * *